United States Patent
Shimp et al.

(10) Patent No.: US 9,597,431 B2
(45) Date of Patent: *Mar. 21, 2017

(54) COMPOSITIONS AND METHODS FOR PROMOTING BONE FORMATION

(71) Applicant: Warsaw Orthopedic, Inc., Warsaw, IN (US)

(72) Inventors: Lawrence A. Shimp, Burlington, WI (US); Keyvan Behnam, Red Bank, NJ (US); Guobao Wei, Milltown, NJ (US); Abdulhafez A. Selim, Cordova, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/274,897

(22) Filed: May 12, 2014

(65) Prior Publication Data

US 2015/0037386 A1    Feb. 5, 2015

Related U.S. Application Data

(63) Continuation of application No. 12/605,746, filed on Oct. 26, 2009, now Pat. No. 8,722,075.

(60) Provisional application No. 61/108,350, filed on Oct. 24, 2008.

(51) Int. Cl.

| | | |
|---|---|---|
| *A61K 35/28* | (2015.01) | |
| *A61K 38/16* | (2006.01) | |
| *A61K 38/17* | (2006.01) | |
| *A61K 38/18* | (2006.01) | |
| *A61K 38/19* | (2006.01) | |
| *A61K 38/22* | (2006.01) | |
| *A61L 27/54* | (2006.01) | |
| *A61K 9/00* | (2006.01) | |
| *A61K 35/32* | (2015.01) | |
| *A61K 38/29* | (2006.01) | |
| *A61L 27/12* | (2006.01) | |
| *A61K 38/20* | (2006.01) | |
| *A61K 31/573* | (2006.01) | |
| *A61K 33/42* | (2006.01) | |
| *A61L 27/36* | (2006.01) | |
| *A61L 27/38* | (2006.01) | |
| *A61F 2/28* | (2006.01) | |

(52) U.S. Cl.
CPC .......... *A61L 27/54* (2013.01); *A61K 9/0024* (2013.01); *A61K 31/573* (2013.01); *A61K 33/42* (2013.01); *A61K 35/32* (2013.01); *A61K 38/177* (2013.01); *A61K 38/1866* (2013.01); *A61K 38/191* (2013.01); *A61K 38/193* (2013.01); *A61K 38/202* (2013.01); *A61K 38/2006* (2013.01); *A61K 38/29* (2013.01); *A61L 27/12* (2013.01); *A61L 27/3608* (2013.01); *A61L 27/3821* (2013.01); *A61F 2/28* (2013.01); *A61F 2002/2817* (2013.01); *A61F 2310/00359* (2013.01); *A61L 2300/258* (2013.01); *A61L 2300/412* (2013.01); *A61L 2300/414* (2013.01); *A61L 2300/426* (2013.01); *A61L 2300/428* (2013.01); *A61L 2300/43* (2013.01); *A61L 2300/45* (2013.01); *A61L 2400/18* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 5,763,416 A | * | 6/1998 | Bonadio et al. | 514/44 R |
| 8,722,075 B2 | * | 5/2014 | Shimp et al. | 424/423 |
| 2010/0303888 A1 | * | 12/2010 | Barralet et al. | 424/425 |

OTHER PUBLICATIONS

Ito et al., 2005, Nature Medicine 11:291-297.*
Le Nihouannen et al., May 2008, Biomaterials 29:3253-3259.*

* cited by examiner

*Primary Examiner* — Elizabeth C Kemmerer

(57) ABSTRACT

A method for promoting bone formation is provided. More specifically, a method for promoting bone formation by promoting osteoclast formation is provided. In one embodiment, an implant comprising an implantable material and an osteoclast stimulating substance is provided.

10 Claims, 4 Drawing Sheets

FIG. 2A  FIG. 2B    FIG. 2C  FIG. 2D
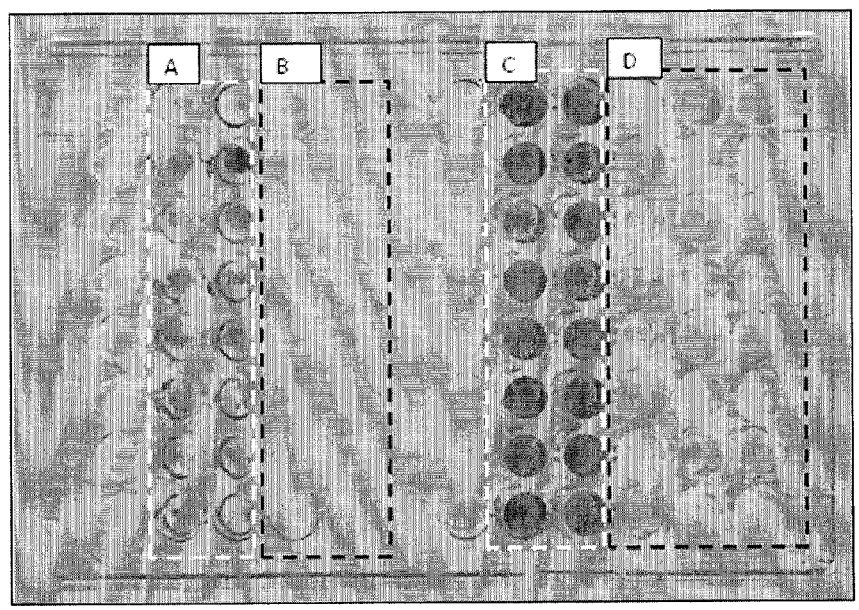
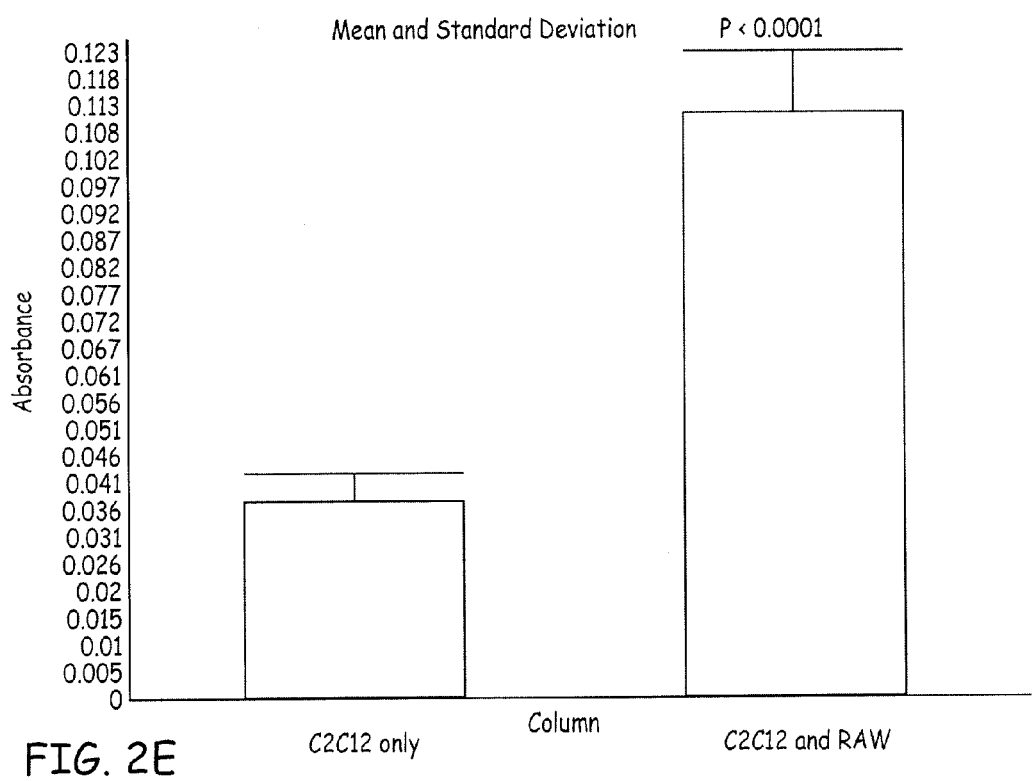
FIG. 2E

COMPOSITIONS AND METHODS FOR PROMOTING BONE FORMATION

This application claims priority to U.S. Provisional Patent Application No. 61/108,350, filed Oct. 24, 2008, entitled "Compositions and Methods for Promoting Bone Formation", the entire content of which is hereby incorporated by reference in its entirety.

FIELD

A method for promoting bone formation is provided. More specifically, a method for promoting bone formation by simulating osteoclasts is provided.

BACKGROUND

Overview of Bone Grafts

Rapid and effective repair of bone defects caused by injury, disease, wounds, or surgery is a goal of orthopaedic surgery. Toward this end, a number of compositions and materials have been used or proposed for use in the repair of bone defects. The biological, physical, and mechanical properties of the compositions and materials are among the major factors influencing their suitability and performance in various orthopaedic applications.

Bone includes various types of cells and an abundant mineralized extracellular matrix. Bone resorption and bone formation are the processes involved in normal body morphogenesis and calcium homeostasis in the body. In addition to its physiological role, bone resorption plays roles in pathological disorders such as osteoporosis, metabolic bone diseases, bone fracture, and malignant hypercalcemia.

Autologous cancellous bone ("ACB"), also known as autograft or autogenous bone, has been considered the gold standard for bone grafts. ACB includes osteogenic cells, which have the potential to assist in bone healing, is non-immunogenic, and has structural and functional characteristics that should be appropriate for a healthy recipient. Some people do not have adequate amounts of ACB for harvesting. These people include, for example, older people and people who have had previous surgeries. Some individuals lack ACB of appropriate dimensions and quality for transplantation, and donor site pain and morbidity associated with the harvesting of ACB can pose serious problems for patients and their physicians.

Much effort has been invested in the identification and development of alternative bone graft materials. Urist published seminal articles on the theory of bone induction and a method for decalcifying bone, i.e., making demineralized bone matrix (DBM). Urist M. R., Bone Formation by Autoinduction, Science 1965; 150(698):893-9; Urist M. R. et al., The Bone Induction Principle, Clin. Orthop. Rel. Res. 53:243-283, 1967. DBM is an osteoinductive material in that it induces bone growth when implanted in an ectopic site of a rodent, owing to the osteoinductive factors contained within the DBM. Honsawek et al. (2000). It is now known that there are numerous osteoinductive factors, e.g., BMP 1-18 (Bone Morphogenetic Protein), which are part of the transforming growth factor-beta (TGF-beta) superfamily. BMP-2 has been widely studied. There are also other proteins present in DBM that are not osteoinductive alone but still contribute to bone growth, including fibroblast growth factor-2 (FGF-2), insulin-like growth factor-I and -II (IGF-I and IGF-II), platelet derived growth factor (PDGF), and transforming growth factor-beta 1 (TGF-beta.1) (Hauschka, et al. 1986; Canalis, et al, 1988; Mohan et al. 1996).

Bone grafting applications are differentiated by the requirements of the skeletal site. Certain applications require a "structural graft" and other applications require an "osteogenic graft." These requirements are not mutually exclusive and some applications may benefit from a structural, osteogenic graft. Grafts may also have other beneficial biological properties, such as, for example, serving as delivery vehicles for bioactive substances. Bioactive substances include physiologically or pharmacologically active substances that act locally or systemically in the host.

A structural graft is a graft in which one role of the graft is to provide mechanical or structural support at the surgical site. Such grafts may contain a substantial portion of mineralized bone tissue to provide the strength needed to be load-bearing. Examples of applications requiring a structural graft include intercalary grafts, spinal fusion, joint plateaus, joint fusions, large bone reconstructions, etc. The biomechanical properties of osteoimplants upon implantation are determined by many factors, including the specific source of the bone used to make the osteoimplant; various physical characteristics of donor tissue; and the method chosen to prepare, preserve, and store the bone prior to implantation, as well as the type of loading to which the graft is subjected.

Mineralized bone may be used in osteoimplants in part because of its inherent strength, i.e., its load-bearing ability at the recipient site. Structural osteoimplants are conventionally made by processing, and then machining or otherwise shaping cortical bones collected for transplant purposes. Osteoimplants may comprise monolithic bone of an aggregate of particles. Further, osteoimplants may be substantially solid, flowable, or moldable. Cortical bone can be configured into a wide variety of configurations depending on the particular application for the structural osteoimplant. Structural osteoimplants are often provided with intricate geometries, e.g., series of steps; concave or convex surfaces; tapered surfaces; flat surfaces; surfaces for engaging corresponding surfaces of adjacent bone, tools, or implants, hex shaped recesses, threaded holes; serrations; etc.

An osteogenic graft is a graft in which one role of the graft is to enhance or accelerate the growth of new bone tissue at the site. Such grafts may contain demineralized bone tissue to improve the osteoinductivity needed for growth of new bone tissue. Examples of applications requiring "osteogenic graft" include deficit filling, spinal fusions, joint fusions, etc.

Bone healing, or remodeling, generally comprises a multi-step process including resorption of existing bone by osteoclasts, formation of new blood vessels, and the subsequent growth of new bone by osteoblasts. Bone resorption and bone formation are thus linked. Bone resorption is generally determined by the rate of osteoclast recruitment and the intensity and duration of osteoclast activity. Starting with osteoclast recruitment, osteoclasts are derived from hemopoietic precursors, for example CFU-M branching off the monocyte macrophage lineage. Agents that stimulate bone resorption in vivo and increase osteoclast formation from bone marrow cultures in vitro and have been implicated in the pathogenesis of osteoporosis include parathyroid hormone and, under certain conditions, IL-6. After bone resorption, the bone remodeling cycle continues into bone formation, using osteoblastic cells.

Osteoclasts function to resorb mineralized bone, dentine, and calcified cartilage. An overview of osteoclast origins and function can be found in "The Osteoclast" (Bone, Vol. 2, B. K. Hall, ed., CRC Press, 1991, 272 pages), incorporated herein by reference. Both mononuclear and multinuclear osteoclasts can resorb bone. Osteoclasts are bloodborne cells originating from hemopoietic mononuclear stem cells or hemopoietic progenitors. The progenitors express some osteoclast-specific genes and proteins, fuse with each other, and differentiate into functionally mature osteoclasts. The differentiation and function of osteoclasts generally are controlled by various osteotropic hormones and local factors. These factors act on osteoclasts and their precursors directly or indirectly via other bone cells. Osteoclasts resorb both the mineral and the organic phases of bone. They generally contain between approximately 1 and approximately 50 nuclei, and range from approximately 20 to over approximately 200 micrometers in diameter. In trabecular bone, they occupy shallow excavations on the surface, and in Haversion bone, they occupy the leading edge of cutting cones. Light microscopic features include irregular cell shape, foamy, acidophilic cytoplasm, a striated perimeter zone of attachment to the bone, and positive staining for tartrate-resistant acid phosphatase. Electron microscopic features are numerous mitochondria, rough endoplasmic reticulum, multiple Golgi complexes, pairs of centrioles in a centrosome, vacuoles, and numerous granules. A ruffled border is located at the interface between resorbing bone surface and the cell surface. Osteoclasts secrete collagenase and acid phosphatase. Carbonic anhydrase is utilized for formation of $H^+$ ions secreted at the ruffled border. The life span of osteoclast work at a trabecular resorption site is about four weeks on average.

Osteoblasts are bone-forming cells. An overview of osteoblast origins and function can be found in "The Osteoblast and Osteocyte" (Bone, Vol. 1, B. K. Hall, ed., CRC Press, 1991, 494 pages), incorporated herein by reference. They produce the organic collagen matrix (and noncollagenous proteins) that undergoes mineralization to form both lamellar and woven bone. Osteoblasts generally originate from marrow stromal cell lineage and appear at bone remodeling sites where osteoclasts previously resorbed bone. Prominent features of osteoblasts are an eccentric nucleus, Golgi apparatus, cell processes, gap junctions, endoplasmic reticulum, and collagen secretory granules.

In healthy bone, bone remodeling, including resorption and formation, is a continuous process. That is, bone resorption, followed by bone formation, occurs continually and in a balanced fashion. More specifically, bone remodeling comprises erosion of bone by osteoclasts, followed by resorption of bone, followed by new bone formation. Overall, each of these processes are part of a surface-based process.

A regulatory system that keeps bone resorption and formation in balance is the RANKL/OPG system (the receptor activator for nuclear factor κ B ligand and osteoprotegerin (OPG) regulatory system). RANKL, a 316-amino acid transmembrane protein, is highly expressed by osteoblast/stromal cells in cancellous (or trabecular) bone. RANKL binds as a homotrimer to RANK (the receptor activator for nuclear factor κ B), a 616-amino acid transmembrane receptor (also a trimer) on the surface of monocyte/macrophage lineage cells, including osteoclasts, and their precursors (pre-osteoclasts). RANKL stimulates osteoclast activity by generating multiple intracellular signals that regulate cell differentiation, function, and survival, such as via ADAM proteins (a disintegrin and metalloprotease). Thus, osteoblasts (bone forming cells) stimulate and contribute to the formation of osteoclasts (cells that break down bone).

Osteoblasts further have a role in regulating formation of osteoclasts. While osteoblasts stimulate osteoclasts by producing and expressing RANKL, osteoblasts also regulate osteoclast formation by secreting OPG, a 380-amino acid-soluble receptor that binds to RANKL and blocks it. Generally, OPG inhibits formation of osteoclasts. In addition to expression by osteoblasts, OPG is expressed by stromal, cardiovascular, and other cells.

Fully differentiated osteoclasts on a bone surface can begin to resorb bone in response to a variety of stimuli, such as for example hormones, cytokines, or adhesion molecules present in the bone matrix or on membranes of other bone cells. The bone-resorbing activity of osteoclasts can be enhanced by some factors produced by osteoblastic UMR cells in response to $1,25(OH)_2D_3$ (Vitamin D), PTH (Parathyroid Hormone), and PTHrP (Parathyroid hormone-related Peptide). Because of the impurity and insufficient number of osteoclasts, investigation of osteoclast activity is generally limited to single-cell studies involving procedures such as electrophysiology, immunocytochemistry, histochemistry, and single-cell molecular techniques.

In the event of trauma to bone, such as from injury or surgery, a wound is created. This disrupts the normal balance of bone turnover to favor bone growth over resorption. The body's initial response to a wound is inflammation, which leads to a temporary increase in the rate of bone resorption through stimulated osteoclast activity as well as generalized macrophage activity (macrophage activity generally being confined to bone particles).

One mechanism for stimulating resorption is through secretion of macrophage colony stimulating factors (MCSF). MCSF can be secreted by various cell types, including adipocytes, vascular endothelial cells, and smooth muscle cells. In combination with RANKL, MCSF can stimulate production of new osteoclasts from osteoclast precursors circulating in the blood. Thus, bone resorption is stimulated by the presence of the additional MCSF induced osteoclasts.

Various other regulating proteins may affect the resorption/formation balance by stimulating expression of RANKL, secretion of MCSF, inhibiting the secretion of OPG (by PTH (parathyroid hormone), for example), and/or carrying out the developmental cascade of cellular events initiated by RANKL and MCSF. Examples of such regulating proteins include, without limitation, ADAM-12 (a disintegrin and metalloprotease-12); PTH; PTHrP; VEGF (vascular endothelial growth factor); Hydrocortisone; 1, 25 dihydroxyvitamin D3; PGE2 (prostaglandin E2); TNFalpha (tumor necrosis factor-alpha); IL-1beta (Interleukin-3 beta), IL-3, IL-6; and bFGF (basic fibroblast growth factor).

Certain types of bone grafts are known to remodel at a slow rate. For example, structural grafts are known to remodel over a period of several years. Increasing the rate of the bone healing process is thus especially beneficial for such types of bone grafts. Conventional approaches to increasing the rate of bone healing, such as those employing demineralized bone and/or growth factors, concentrate primarily on increasing osteoblast activity, i.e., increasing the rate of bone formation. Such approaches do not directly take advantage of the impact of resorption and remodeling in the bone healing process. Accordingly, to stimulate the bone resorption rate, and thus the overall rate of bone healing, osteoclast activity may be stimulated by supplying MCSF, RANKL, and/or various other regulating proteins to a wound site.

BRIEF DESCRIPTION OF FIGURES

FIGS. 2A and 2B depict C2C12 control cultures.

FIGS. 2C and 2D depict RAW mononuclear cells administered to C2C12 cell cultures.

FIG. 2E depicts absorbance of RAW/C2C12 cultures as compared to the C2C12 only cultures after alkaline phosphatase staining.

BRIEF SUMMARY

Figure 1:
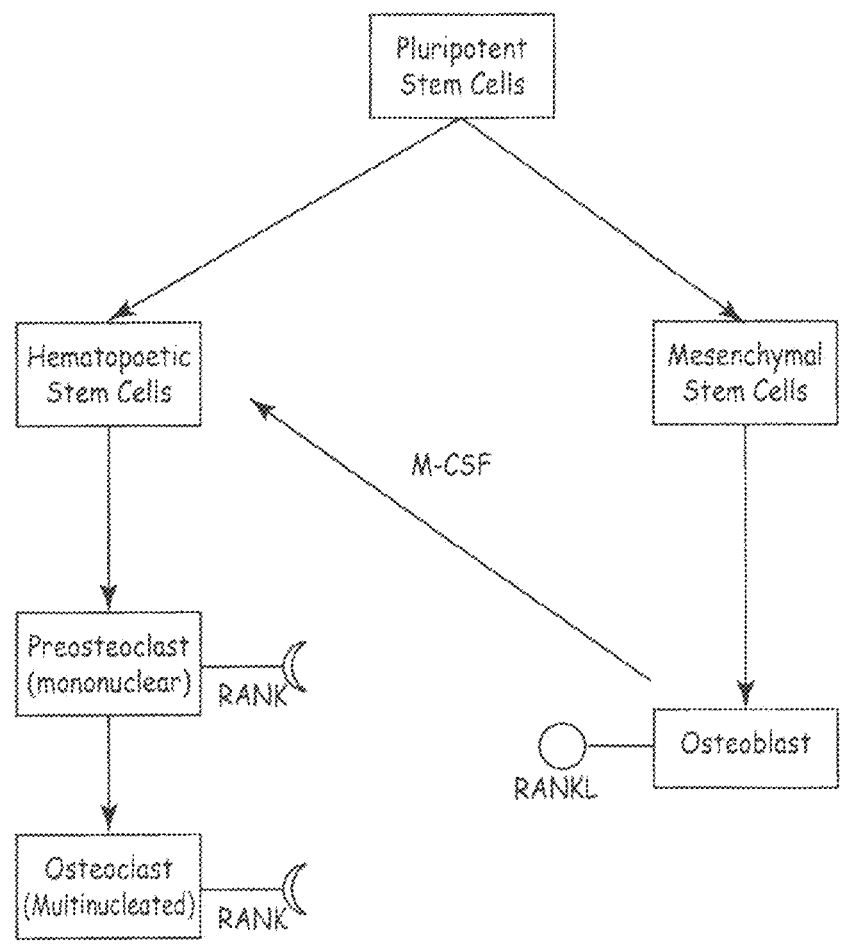
FIG. 1 depicts a schematic representation of osteoclast and osteoblast differentiation and signaling.

A method for promoting bone formation is provided. Bone remodeling comprises bone erosion by osteoclasts, known as resorption, followed by bone formation. Due to the coupling of these resorption and formation activities in normal bone biology, the initiation of bone resorption can trigger formation events. A method for promoting bone formation by promoting osteoclast formation (osteoclastogenesis), and thus erosion of bone to ultimately stimulate bone formation, is provided. In some embodiments, a method for promoting bone formation by promoting osteoblast formation is provided. In other embodiments, a method for promoting bone formation by enhancing the bone-resorbing activity of osteoclasts is provided. In some embodiments, osteoclast and osteoblast formation are promoted with or without enhancement of osteoclast activity.

An implant for promoting bone formation is provided. In one embodiment, the implant comprises an implantable material and a stimulating substance, wherein the stimulating substance stimulates osteoclast formation in vivo.

A method of forming an implant is further provided. In one embodiment, the method comprises providing an implantable material, providing a stimulating substance, wherein the stimulating substance stimulates osteoclast formation in vivo or that enhances the bone-resorbing activity of osteoclasts in vivo, and combining the stimulating substance with the implantable material.

While multiple embodiments are disclosed, still other embodiments of the present invention will become apparent to those skilled in the art from the following detailed description. As will be apparent, the method disclosed herein is capable of modifications in various obvious aspects, all without departing from the spirit and scope of the present teachings. Accordingly, the detailed description is to be regarded as illustrative in nature and not restrictive.

DETAILED DESCRIPTION

Definitions

Biocompatible, as used herein, is intended to describe materials that, upon administration in vivo, do not induce undesirable long-term effects.

Bone, as used herein, refers to bone that is cortical, cancellous, or cortico-cancellous bone of autogenous, allogenic, xenogenic, or transgenic origin.

Inflammation, as used herein, is the first response of the immune system to infection or irritation. As used herein, inflammation refers to a tissue reaction characterized by the presence of multinucleated giant cells without infection being present.

Osteoblast formation, as used herein, refers to any process that brings (or recruits) osteoblasts to a site or causes osteoblasts to form at a site. Such process may include differentiation, recruitment, elaboration, and activation. Osteoblast formation is intended to refer to processes leading to formation of osteoblasts from other cells, such as pluripotent cells, stem cells, progenitor cells, pre-osteoblast. Osteoblast formation may also refer to processes of recruiting or attracting osteoblasts to a site and/or inducing the osteoblastic division (mitosis). Generally, osteoblast formation refers to any process that may lead to osteoblasts making new tissue at a site. Osteoblast formation may also be referred to as osteoblast production.

Osteoclast formation, as used herein, refers to any process that brings (or recruits) osteoclasts to a site or causes osteoclasts to form at a site. Such process may include osteoclast recruitment (chemotaxis, migration), osteoclast differentiation within the hemopoietic lineage or from pre-osteoclasts, and osteoclast activation. Osteoclast formation also refers osteoclast fusion in the formation of multinucleated osteoclasts. Osteoclast formation also includes any process leading to osteoclast erosion of bone at a site. As used herein, "osteoclast formation," "osteoclast recruitment," and "osteoclast production" are used interchangeably.

Osteoconductive, as used herein, refers to the ability of a non-osteoinductive substance to serve as a suitable template or substance along which bone may grow.

Osteogenic, as used herein, refers to the ability of an agent, material, or implant to enhance or accelerate the growth of new bone tissue by one or more mechanisms such as osteogenesis, osteoconduction, and/or osteoinduction.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., 1998. In other instances, osteoinduction is considered to occur through cellular recruitment and induction of the recruited cells to an osteogenic phenotype.

Precursor or progenitor, as used herein, refers to a cell that may become, form, or differentiate into a more mature cell-type. An osteoclast precursor may be a pre-osteoclast or a hemopoietic lineage derived cell.

Remodeling, as used herein, refers to a process by which implanted tissue is replaced by similar host tissue. Bone remodeling comprises two stages: bone resorption and bone formation.

Resorption, as used herein, refers to a process by which the implanted tissue is resorbed by the body and effectively disappears. Resorption may be the first stage of remodeling if followed by formation of host tissue similar to the implanted tissue.

Stimulating Substance, as used herein, refers to any substance, such as a protein, chemical compound, or cell that stimulates osteoclast formation by participating in the developmental cascade of cellular events resulting in osteoclast formation or enhancing the bone-resorbing activity of osteoclasts.

I. Overview

A method for promoting bone formation is provided. More specifically, a method for promoting bone formation by promoting osteoclast formation, or by enhancing the bone resorbing activity of osteoclasts, is provided. A method for stimulating osteoclasts and associated resorption to stimulate remodeling of bone is thus provided.

Osteoclasts are blood-borne cells derived from hemopoietic mononuclear stem cells or hemopoietic progenitors. The progenitors fuse with each other, and differentiate into functionally mature osteocytes. Cells in osteoclast and osteoblast lineages communicate with each other through cell-cell contact, diffusible paracrine factors and cell-bone matrix interaction. Osteoclast-osteoblast communication occurs in a basic multicellular unit (BMU) at the initiation, transition and termination phases of bone remodeling. At the initiation phase, hemopoietic precursors are recruited to the BMU. These precursors express cell surface receptors including c-Fms, RANK, and costimulatory molecules, such as osteoclast-associated receptor (OSCAR), and differentiate into osteoclasts following cell-cell contact with osteoblasts, which express ligands. Bidirectional signaling is generated by interaction between ephrinB2 on osteoclasts and EphB4 on osteoblast precursors facilitates the transition. (Matsuo K, Irie N., *Osteoclast-Osteoblast Communication*, Arch Biochem Biophys. 2008 May 15; 473(2):201-91.)

Bone callus formation depends on osteoblastic new bone apposition and osteoclastic resorption activity. During the remodeling phase, osteoclasts are very active. A major paradigm of osteoclast biology has emerged with the discovery of the receptor activator nuclear factor kB (RANK), its ligand (RANKL), and osteoprotegerin (OPG), which are heavily involved in bone resorption, regulating osteoclast activity. RANK is a membrane receptor on osteoclasts and immune system cells, and binding with RANKL is necessary to promote differentiation, survival and activation of osteoclastic cells.

Recently, Marchelli et al. demonstrated that, in patients with atrophic nonunion shaft fractures, the mean serum OPG level was significantly increased with respect to healed and healing controls. The significantly higher serum OPG level in the patients may suggest an imbalance in the RANK/RANKL/OPG system, with osteoclast downregulation (Marchelli D, et al., J. Orthop. Traumatol., 2009 June; 10(2): 55).

Moreover, Gerstenfeld et. al. demonstrated that osteoclast inhibitors (alendronate and denosumab) delayed the removal of cartilage and the remodeling of the fracture callus in unilateral transverse femur fractures mice (Gerstenfeld L C, et al., J. Bone. Miner. Res., 2009 February; 24(2): 196-208).

Bone remodeling comprises bone erosion and resorption by osteoclasts, followed by bone formation by osteoblasts. The method provided herein comprises stimulating osteoclast production, and thus resorption of bone, to stimulate remodeling of bone, including new bone formation. In further embodiments, the bone resorbing activity of osteoclasts may be enhanced. In alternative embodiments, a method provided herein comprises stimulating osteoclast production, in lieu of or in addition to osteoblast production, to stimulate remodeling of bone. Osteoblasts may be stimulated by known methods, including but not limited to those described in WO/2005/123191; Andress, *IGF-binding protein-5 stimulates osteoblast activity and bone accretion in ovariectomized mice*, Am. J. Physiol. Endocrinol. Metabl., Vol. 281, Issue 2, E283-288, August 2001, both incorporated by reference herein. An implant may be provided for stimulating osteoclast production, osteoclast enhancement, and/or osteoblast production, and, thereby, bone remodeling and formation. The implant may include one or more stimulating substances for stimulating osteoclast production or enhancing the resorbing activity of osteoclasts. The implant may further include one or more stimulating substances for stimulating osteoblast production. In contrast to conventional approaches for stimulating bone growth by increasing substantially only osteoblast activity, stimulating osteoclast activity takes advantage of the resorption and remodeling aspect of bone healing. In some embodiments, an implant may be provided that stimulates osteoclast production and also stimulates osteoblast production.

The implant may comprise any suitable material for implantation in the body, as is described more fully below. Generally, the implant may comprise any natural or synthetic structure (bone, tissue, protein, carbohydrate, polymer, or other) or combination of these. For example, the implant may comprise bone or a polymer, such as those described in U.S. Pat. Nos. 6,294,187 and 6,696,073, which are incorporated by reference herein for all purposes. The implant may comprise bone material, such as described in U.S. patent application Ser. No. 12/140,044 and U.S. Patent Publications Nos. 2007/0098756 and 2007/0110820 all for Bone Matrix Compositions and Methods, herein incorporated by reference in their entireties. In embodiments wherein the implant comprises bone, the bone may be autogenic, allogenic, xenogenic, transgenic, or genetically engineered. Further, the bone may be obtained utilizing methods known in the art, e.g., allogenic donor bone. Bone-derived elements can be readily obtained by various suitable methods, e.g., as described in U.S. Pat. No. 6,616,698, incorporated herein by reference.

An implant comprising an implant material and at least one stimulating substance is thus provided. When implanted, the implant stimulates osteoclast production, thereby stimulating the resorption process and increasing the speed of bone remodeling and graft incorporation. Generally, in some embodiments, the implant may generate a protein release curve that provides osteoclast stimulation over a period of time. In some embodiments, an implant provided herein may stimulate osteoblast production in addition to or in lieu of osteoclast production.

To reduce the potential for osteoclast stimulating factors producing detrimental effects in various parts of the skeleton, the osteoclast stimulating factors may be placed in the surgical site on a carrier such that their release is localized, in terms of time, location, or both. This may provide for osteoclast activity being localized on the surgical implant, while the growth factors released by the osteoclasts can travel throughout the graft site and stimulate osteoblasts, mainly within the graft site. Any suitable carrier may be used for the osteoclast stimulating factors, including materials such as a polymer, a ceramic, a tissue such as bone, or combinations of these. The material may release the stimulating factor(s) slowly, such that they are mainly taken up by osteoclasts close to the material. Alternatively, the factors also may be released mainly by the action of osteoblasts. A material such as a calcium phosphate ceramic or cortical bone (allograft or xenograft) is slowly resorbed by osteoclasts. If the stimulating factor is within the calcium phosphate ceramic or cortical bone, then osteoclast activity may release the stimulating factor, encouraging more rapid osteoclast activity and more rapid resorption of the material. This may assist in localizing osteoclast activity. In addition, this can be advantageous to the graft healing as a whole because a material that normally will persist for years can be made to remodel in a shorter time, thus hastening the full healing of the site. In addition, the osteoclast stimulating substances also may be released by cells that have been engineered to contain osteoclast-related DNAs, RNAs or siRNAs (small interfering RNAs). Thus, the factor release profiles may be controlled by gene incorporation and transfection/transformation efficiency.

II. Provide Implantable Material

In various embodiments, any suitable implantable material may be used for the implant. Suitable materials include, without limitation, any natural or synthetic structure (bone, tissue, protein, carbohydrate, polymer, or other) or combination of these that can be used to form a biocompatible implant. In some embodiments, the implant comprises fully mineralized bone. In alternative embodiments, the implant comprises calcium phosphate mineral, the calcium phosphate mineral being synthetic, non-synthetic, or derived from bone. Generally, the implant may comprise bone (autogenic, allogenic, xenogenic, transgenic; mineralized, demineralized, or partially demineralized), a polymer (such as polyalkylenes (e.g., polyethylenes, polypropylenes, etc.), polyamides, polyesters, polyurethanes, poly(lactic acid-glycolic acid) (PLGA), poly(lactic acid) (PLA), poly(glycolic acid) (PGA), poly(glaxanone), poly(orthoesters), poly(pyrolicacid), poly(phosphazenes), polycarbonate, other bioabsorbable polymer such as Dacron or other known surgical plastics, a natural biologically derived material such as collagen (including known collagen materials and collagen materials as disclosed in U.S. patent application Ser. No. 12/030,181, filed Feb. 12, 2008, hereby incorporated by reference in its entirety), gelatin, chitosan, alginate, a ceramic (with bone-growth enhancers, hydroxyapatite, etc.), PEEK (polyether-etherketone), desiccated biodegradable material, metal, composite materials, a biocompatible textile (e.g., cotton, silk, linen), extracellular matrix components, tissues, or composites of synthetic and natural materials, or other.

The material of the implant may be chosen to exhibit certain properties, such as structural, support, radiopaque, or other properties. Example materials include surface demineralized bone, optionally of a predetermined particle size, demineralized bone fibers, optionally pressed, and/or allograft. For embodiments wherein the substance is biologic, the substance may be autogenic, allogenic, xenogenic, or transgenic. Other suitable materials include, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, demineralized bone matrix, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above. In accordance with one embodiment, the material may be an osteoinductive bone matrix composition such as those described in U.S. patent application Ser. No. 12/140,044 and U.S. Patent Publications Nos. 2007/0098756 and 2007/0110820 all for Bone Matrix Compositions and Methods, herein incorporated by reference in their entireties. A material for implants as provided may be homogenous, or generally a single substance, or may be heterogeneous, or a mixture of substances.

The implant may be of various shapes, forms, structures, and load bearing ability. Suitable collagen materials for use as implant materials may be formed from dispersions of human collagen as disclosed in U.S. patent application Ser. No. 11/673,972, U.S. patent application Ser. No. 12/030,188, PCT Application No. PCT/US2008/053763, and PCT Application No. PCT/US2009/33799, all herein incorporated by reference. The implant may comprise a shape-retaining solid made of loosely adhered particulate material, e.g., with collagen. It may also comprise a molded, porous solid, or simply an aggregation of close-packed particles held in place by surrounding tissue. See, e.g., U.S. Pat. Nos. 6,863,694, 6,843,807, 6,808,585, 6,294,041, 6,123,731, and 5,899,939, all herein incorporated by reference in their entireties for all purposes. Masticated muscle or other tissue may also be used. In some embodiments, the implant may comprise a settable and/or injectable material, such as, for example, a polymeric cement, a settable calcium phosphate, a settable poly vinyl alcohol, a polyurethane, or a liquid settable polymer. Suitable settable calcium phosphates are disclosed in U.S. Pat. Nos. 5,336,264 and 6,953,594, which are hereby incorporated by reference. Further, biocomposites may be used. Suitable materials for preparing biocomposites are disclosed in U.S. Patent Publication Nos. 2007/0191963, 2006/0216323, and 2005/0251267, U.S. Pat. Nos. 6,696,073, 6,478,825, 6,440,444, and 6,294,187, all herein incorporated by reference in their entireties for all purposes. U.S. Pat. Nos. 7,323,193, 7,163,691, 6,863,694, 6,808,585, 6,616,698, 6,599,520, 6,436,138, 5,676,146, 5,510,396, 5,507,813, 5,484,601, 5,439,684, 5,405,390, 5,314,476, 5,298,254, 5,290,558, 5,284,655, 5,236,456, 5,073,373, U.S. Patent Application Publications Nos. 2007/0098756, 2007/0110820; 2007/0154563; 2009/0130173, and 2009/0192474 and U.S. patent application Ser. Nos. 12/171,168; 12/205,539; 12/140,062; 12/267,985; 12/140,025; 12/267,985; 12/254,619; 61/108,350, 61/152,057; 61/154,673; 61/154,679, and 61/154,689 also are herein incorporated by reference in their entireties.

The material of the implant may be selected and treated such that it releases materials during degradation. Thus, bone morphogenic proteins (BMPs), growth factors, antibiotics, angiogenesis promoting materials (discussed more fully below), bioactive agents (discussed more fully below), or other actively releasing materials may be incorporated into the implant material such that as the implant is resorbed in the body, the actively releasing material is released. For example, an actively releasing material may be incorporated into a biodegradable polymer implant such as one manufactured of a biodegradable polyester such as poly(lactic acid) (PLA), poly(glycolic acid) (PGA), or poly(lactic-co-glycolic acid) (PLGA). In some embodiments, poly(ethylene glycol) (PEG) may be incorporated into the biodegradable polyester to add hydrophilic and other physico-chemical properties to enhance drug delivery.

In some embodiments the implant may include one or more other components, for example, binders, adhesives, fillers, biologically active components, reinforcing components or reinforcing structures, and coupling agents, as described in U.S. Pat. No. 6,399,693, the contents of which are incorporated by reference herein. Further exemplary implants may contain particles, powders, granules, fibers, strips and/or larger pieces of xenogenic, allogenic, transgenic, engineered, and/or autologous cortical and/or cancellous bone, and other minerals, compounds, and binding agents as described in U.S. Pat. No. 6,478,825, the contents of which are incorporated by reference herein. Implants may also comprise polymers, biological-based polyurethanes, inorganic ceramics, and calcium phosphate materials as described in U.S. Pat. No. 7,291,345, and U.S. Publication No. 2006/0216323, which are incorporated by reference herein.

The implant may be shaped. Shaped implants may be created by various methods that can be used, individually or in combination to provide an implant of a desired size and configuration. For example, shaped implants and methods of shaping implants are discussed in U.S. Pat. No. 6,696,073, incorporated by reference herein.

In accordance with some embodiments, the material of the implant may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder as described in U.S. Pat. No. 5,073,373; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. The drug may be a synthetic or naturally occurring drug. The drug may be a small or large molecule, peptide, nucleotide or a combination thereof. In some embodiments, the bioactive agent may be a growth factor, cytokine, extracellular matrix molecule, or a fragment or derivative thereof, for example, a protein or peptide sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmcopeial Convention, Inc., Rockville Md., 2001.

The description herein focuses on embodiments wherein the implant comprises mineralized bone. It is to be appreciated that this is for illustrative purposes only and is not intended to be limiting.

III. Provide at Least One Stimulating Substance

A stimulating substance is provided. The stimulating substance may be any substance, such as a protein, peptide, hormone, nucleotide, small molecule, large molecule or a combination thereof, that participates in, stimulates, or affects a signaling cascade leading to osteoclast formation. The stimulating substance may alternatively be any substance that enhances the bone resorbing activity of osteoclasts. In some embodiments, the stimulating substance may alternatively or additionally stimulate osteoblast formation. The stimulating substance may also increase osteoclast division or fusion. In some embodiments the stimulating substance may enhance osteoclast maturation, or prolong osteoclast lifespan. The stimulating substance may be selected because it directly stimulates osteoclast activity, or it may be selected because of its ability to compete with, inactivate, bind, or down-regulate factors or cells that inhibit osteoclast formation or activity. For example, the substance may decrease secretion of OPG or other osteoclast-inhibitors, thereby preventing the inhibition of osteoclast formation. Accordingly, broadly speaking, the stimulating substance may be an "osteoclast stimulator" or "anti-osteoclast-inhibitor".

Proteins that directly stimulate osteoclast activity may stimulate secretion of MCSF or other proteins secreted further down the cascade, such as an ADAM protein, for example ADAM-12. Exemplary stimulating substances that stimulate osteoclast activity include MCSF, RANKL, ADAM-12, interleukins (IL-1 beta, IL-3, IL-6, IL-11), and bFGF. Another example, which may have application further down the signaling cascade, is IL-3. IL-3, in the presence of 1,25 dihydroxyvitamin D3 and/or PGE2 (prostaglandin E2), may lead to the expression of calcitonin (CT) receptors on osteoclasts and thus contributes to the maturation of osteoclasts. Other pathways independent of the RANK-MCSF system may be initiated by TNF-alpha (tumor necrosis factor alpha), and or VEGF (vascular endothelial growth factor).

In some embodiments, the stimulating substance may selectively bind and/or inactivate factors that inhibit osteoclast formation or osteoclast activity. For example, the implant material may contain an anti-OPG antibody, fragment, or other OPG binding protein. In some embodiments the stimulating substance may be a polymer that selectively binds an inhibitory factor.

Adhesion, recruitment, or retention of preosteoclast cells at an injury or implant site may aid osteoclast formation and stimulation. Both TNF alpha and IL-1 promote cell adhesion in the injured bone site by stimulating microvascular endothelial cells to capture pre-osteoclast cells. Other suitable stimulators of osteoclastic cell formation include parathyroid hormone, parathyroid-hormone-related peptide, thyroid hormones, macrophage colony-stimulating factor, granulocyte-macrophage colony-stimulating factor, tumor necrosis factor-alpha, transforming growth factor-alpha and epidermal growth factor, leukotrienes, Vitamin A, Insulin-like growth factor-I, Hepatocyte growth factor, bone morphogenetic protein-2, and postaglandin E.

Osteoblastic stromal cells may affect differentiation of osteoclast progenitors into osteoclasts through a mechanism of cell-to-cell interaction/signaling. Osteotropic hormones and cytokines regulate the differentiation of precursor cells into osteoclasts. Differentiation of osteoclast precursors into osteoclasts may be regulated by at least three independent signal transduction pathways: $1\alpha,25(OH)_2D_3$-, cAMP-, and gp130-mediated signals. Target cells for osteotropic hormones and cytokines may be osteoblastic cells. Osteoblastic cells may produce factors which induce or stimulate osteoclast differentiation in response to osteotropic hormones and cytokines. Osteoblastic cells also produce some soluble factors such as M-CSF and the complement C3, which regulate osteoclast development. M-CSF has roles in proliferation and differentiation of osteoclast progenitors, as well as in migration, chemotaxis, and survival of mature osteoclasts. Accordingly, stimulating substances may affect osteoblastic stromal cells, osteotropic hormones, and cytokines.

Molecular factors that stimulate bone resorption can also stimulate bone formation. Exemplary proteins that decrease secretion of OPG include PTH and hydrocortisone. For example, hydrocortisone stimulates osteoclast activity by inhibiting the production of OPG, and is known to cause bone resorption as a side effect of its use.

In various embodiments, the stimulating substance can be a nucleic acid or nucleic acid containing compound. The nucleic acid can have an associated nuclear localization signal to deliver agents into the target cell nucleus. The nucleic acids may be single stranded or double stranded, or contain portions of both double stranded or single stranded sequence. The nucleic acid may be DNA, both genomic and cDNA, RNA or hybrid, where the nucleic acid contains any combination of deoxyribo- and ribonucleotides, and any combination of bases, including uracil, adenine, thymine, cytosine, guanine, and any of known base analogs, including, but not limited to, 4-acetylcytosine, 8-hydroxy-N-6-methyladenosine, aziridinylcytosine, pseudoisocytosine, 5-(carboxyhydroxymethyl)uracil, 5-fluorouracil, 5-bromouracil, 5-carboxymethylaminomethyl-2-thiouracil, 5 carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracils, 5-methoxyaminomethyl-2-thiouracil, beta-D-mamino-sylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

In one aspect the nucleic acids comprise functional nucleic acids, where "functional nucleic acid" refers to any bioactive nucleic acid. A functional nucleic acid may have enzymatic function, regulate transcription of nucleic acids, regulate the translation of an mRNA so as to interfere with the expression encoded protein, or affect other physiological processes in the cell. Functional nucleic acids include, by way of example and not limitation, ribozymes, antisense nucleic acids, decoy oligonucleotide nucleic acids, and interfering RNAs (RNAi). These also include short interfering RNA (siRNA).

In various embodiments, nucleic acids, DNAs and/or RNAs, may encode the above osteoclast stimulating proteins can be incorporated into the implants. The DNA or RNA may be engineered to code for the entire protein or only part of the protein. In some embodiments the nucleic acids may be combined with amino acids or other molecules to aid in uptake by cells in vivo. In various embodiments this uptake of nucleic acids may result in either transient or stable expression.

Stimulating substances can include non-coding nucleic acids, DNAs, RNAs, and nucleoproteins. These stimulating substances may affect osteoclast and/or osteoblast formation and/or activity. In various embodiments the stimulating substance may be, for example, an interfering RNA (RNAi) that may down-regulate expression of a factor that inhibits osteoclast formation. Such implants may contain for example, siRNA directed to factors that either prevent osteoclast formation or reduce osteoclast activity. These nucleic acids may be referred to as "anti-sense nucleic acids," and comprise nucleic acids, particularly in the form of oligonucleotides, characterized as hybridizing to the corresponding complementary or substantially complementary nucleic acid strand to inhibit expression of the gene encoded by the complementary strand.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. Generally, short oligonucleotides, of from 7 to 8 bases in length, can be strong and selective inhibitors of gene expression (see, e.g., Wagner et al., Nature Biotechnol. 14:840-844 (1996)).

Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation. The antisense nucleic acids may be directed to any expressed protein, including, by way of example and not limitation, to receptors, hormones, signaling molecules, peptides, and transmembrane proteins.

In various embodiments the stimulating substance may be cells, or cells may be added in addition to the stimulatory substance. For example, cells may also be combined with the implant material prior to implantation. In some embodiments the cells may be osteoclast precursor cells. In other embodiments the cells may induce osteoclast differentiation or stimulate osteoclast activity. In still other embodiments the cells may be stromal cells, osteoblasts or osteoblast precursors including mesenchymal cells.

In some embodiments cells may be added to the implant material that contain versions of, or extra copies of, genes that encode stimulating substances. For example, engineered cells may be combined with the implants such that they secrete, express, or produce the stimulating substance. These cells may then produce the osteoclast stimulating substance, including proteins or other molecules, locally.

Stimulating substances may alternatively be materials that decrease formation of, or inhibit, osteoclast inhibitors. Such anti-osteoclast-inhibitor may include materials that reduce formation or activity of calcitonin, calcitonin-related peptides, estrogens and androgens, glucocorticoids, interferon-γ, and interleukin-4. In further embodiments, stimulating substances may include substances that stimulate osteoblasts, such as growth factors and other inductive materials. Such substances may affect differentiation of stem cells into osteoblasts. Any of the substances identified above, other stimulating substances, and mixtures and combinations of these may be used in the present invention.

IV. Apply the at Least One Stimulating Substance to the Implant Material

In some embodiments, the implant is provided with at least one stimulating substance. Such substances may be added directly to the implant material or added as a mixture to the implant material. The substance may be associated with a suitable carrier material capable of maintaining the substances at an in vivo site of application. The carrier may be biocompatible, in vivo biodegradable, and sufficiently porous to allow cell infiltration.

In one embodiment, at least one stimulating substance is added to an implant comprising a mineralized component such as mineralized bone, calcium phosphate, or calcium sulfate. In another embodiment, at least one stimulating substance is added to an implant through incorporation of the stimulating substance into a component included with the implant. The component may be designed and configured for delivery of the protein. Such components may include, for example, DBM or a polymer matrix.

In some embodiments, the implant may comprise a mixture of a mineralized component and a matrix such as a hydrogel, polymer, collagen, or faster resorbing mineral such as calcium sulfate. The mixture may be developed to generate a protein release curve that provides osteoclast stimulation over a period of time. At least one stimulating substance may be provided with the mixture. Various methods for delivering a substance may be used including, for example encapsulation and microencapsulation, and attachment of the molecule into a resorbable polymer such that the drug becomes eluted as the polymer resorbs. Reference is made to "polymerdrugs" (e.g., http://rutchem.rutgers.edu/content_dynamic/faculty/kathryn_uhrich.shtml). Other methods include lyophilization of the material onto the surface and immobilization (such as by chemical attachment) of the substance onto the surface.

The stimulating substance may be added to a carrier to form a substance mixture and the mixture may be used to coat the implant. The implant may be impregnated with the substance by soaking the implant in a substance bath, which bath may be a dispersion, solution, or any other mixture of the substance and a liquid or gas. The implant material may be particulated and added to a carrier and the substance may also be added to the carrier.

V. Form an Implant

The implant may be shaped, molded, and/or deformable. The implant may comprise a monolithic implant or an aggregate of smaller elements. The implant may assume a determined or regular form or configuration such as a sheet, plate, disk, tunnel, cone, tube, or other. Prefabricated geometry may include, but is not limited to, a crescent apron for single site use, an I-shape to be placed between teeth for intra-bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, or wave plates. Partial tubular as well as flat plates can be fabricated from the bone graft. Such plates may include such conformations as, e.g., concave contoured, bowl shaped, or defect shaped. The implant can be machined or shaped by any suitable mechanical shaping means. Computerized modeling can provide for the intricately-shaped three-dimensional architecture of an implant custom-fitted to a bone repair site with great precision. The implant may have fixation elements or other geometries customized to the placement of the implant in vivo. In embodiments wherein the implant is shaped or moldable, the implant may retain coherence in fluids.

Generally, monolithic implants are suitable for machining to specific dimensions or configurations. Implants comprising an aggregate of materials may be molded and/or machined, as described above. Alternatively, such an aggregate implant may be extruded or otherwise formed. In one embodiment, an implant formed of an aggregate of mineralized bone particles may be formed by combining the mineralized bone particles with a carrier and molding the combination carrier and mineralized bone particles. The molded carrier and mineralized bone particles can further be machined. In some embodiments, the implant may be formed as a gel or paste. Generally, useful DBM implants are disclosed in U.S. Pat. Nos. 5,073,373; 5,284,655; 5,290,558; 5,314,476; 5,507,813; 5,510,396; and 5,676,146, each of which is incorporated by reference herein.

In accordance with one embodiment, the implant comprises large segmental allograft pieces, for example osteochondral or other generally large pieces of allograft. Such implant may be used for tumor reconstruction and trauma. In accordance with a specific embodiment, the large segmental allograft pieces are mineralized bone.

In some embodiments, the implant may be provided within another structure or covering, such as a mesh bag or a cage (see references incorporated by reference above). Such implant provided in a covering may be substantially cohesive, moldable, injectable, solid, flowable, or particulated. For example, a plurality of bone segments including a stimulating substance may be placed in the covering such that the covering retains bone segments that would otherwise be loose and non-cohesive.

In some embodiments, the implant is a structural implant and thus may have a configuration suited for a load-bearing position in vivo. For example, the implant may comprise a contiguous scaffold of cortical bone or dense hydroxyapatite. Cortical bone can be configured into a wide variety of configurations depending on the particular application for the structural osteoimplant. Structural osteoimplants are often provided with intricate geometries, e.g., series of steps; concave or convex surfaces; tapered surfaces; flat surfaces; surfaces for engaging corresponding surfaces of adjacent bone, tools, or implants, hex shaped recesses, threaded holes; serrations, etc.

Accordingly, in various embodiments, the implant be monolithic or may comprise an aggregate of particles. The implant may be substantially solid, flowable, or moldable. The implant may be substantially cohesive or may comprise a plurality of segments, for example retained by a covering.

VI. Optional Additives

Optionally, other additives may be provided with the implant. It will be appreciated that the amount of additive used may vary depending upon the type of additive, the specific activity of the particular additive preparation employed, and the intended use of the implant. The desired amount is readily determinable by the user. Any of a variety of medically and/or surgically useful optional substances can be incorporated in, or associated with, the tissue, before, during, or after treatment.

In certain embodiments, the additive is adsorbed to or otherwise associated with the implant. In certain embodiments, the additive is attached to the implant using a linker so that the additive is free to associate with its receptor or site of action in vivo. In other embodiments the additive is either covalently or non-covalently attached to the implant. An additive may be provided within the implant in a sustained release format. For example, the additive may be encapsulated within biodegradable nanospheres, microspheres, etc.

Suitable additives include angiogenesis promoting materials, bioactive agents, medically/surgically useful substances, and osteoinducing agents. It will be understood by those skilled in the art that the lists of optional substances herewith included are not intended to be exhaustive and that other materials may be provided with the implant disclosed herein.

Osteoinducing Agents

Other osteoinducing agents besides the stimulating substances may be added to the implant. These agents may be added in an activated or non-activated form. These agents may be added at anytime during the preparation of the implant.

Osteoinducing agents include any agent that leads to or enhances the formation of bone. The osteoinducing agent may do this in any manner, for example, the agent may lead to the recruitment of cells responsible for bone formation, the agent may lead to the secretion of matrix which may subsequently undergo mineralization, etc. Suitable osteoinducing agents include BMPs, transforming growth factor (TGF-0), etc. In one embodiment, the inducing agent is genetically engineered to comprise an amino acid sequence which promotes the binding of the inducing agent to the implant. Sebald et al., PCT/EPOO/00637, incorporated herein by reference, describe the production of exemplary engineered growth factors suitable for use with DBM.

VII. Uses

The implant may be applied at a bone repair site, for example, a site resulting from injury, defect brought about during the course of surgery, infection, malignancy, or developmental malformation. In some embodiments, the implant may be applied at a site wherein the implant has a load-bearing function. The implant may be used for treatment of metabolic bone disease, bone healing, cartilage repair, spinal disc repair, tendon repair, repair of a defect created by disease or surgery, dural repair and may be further used in a wide variety of orthopedic, periodontal, neurosurgical, and oral and maxillofacial surgical procedures. Examples of applications requiring a structural graft include intercalary grafts, spinal fusion, joint plateaus, joint fusions, large bone reconstructions, etc. Large implants having osteoclast stimulating properties may contribute to the healing process. The implant may further be used in veterinary applications.

The implant may further be used as drug delivery device, for example, to deliver factors or agents that promote wound healing. The implant may alternatively or additionally be used to deliver other pharmaceutical agents including antibiotics, anti-neoplastic agents, growth factors, hemopoietic factors, nutrients, other bioactive agents described above, etc. The amount of the bioactive agent included with the implant can vary widely and will depend on such factors as the agent being delivered, the site of administration, and the patient's physiological condition. The optimum levels is determined in a specific case based upon the intended use of the implant.

At the time just prior to placement of the implant in a defect site, optional materials, e.g., autograft bone marrow aspirate, autograft bone, preparations of selected autograft cells, autograft cells containing genes encoding bone promoting action, etc., can be combined with the implant. The implant can be implanted at the bone repair site, if desired, using any suitable affixation means, e.g., sutures, staples, bioadhesives, screws, pins, rivets, other fasteners and the like or it may be retained in place by the closing of the soft tissues around it.

VIII. Examples

Example 1

This example shows that providing pre-osteoclast results in mesenchymal differentiation. Osteoclasts are blood-borne cells derived from hemopoietic mononuclear stem cells or hemopoietic progenitors. The progenitors fuse with each other, and differentiate into functionally mature osteocytes. Cells in osteoclast and osteoblast lineages communicate with each other through cell-cell contact, diffusible paracrine factors and cell-bone matrix interaction. Osteoclast-osteoblast communication occurs in a basic multicellular unit (BMU) at the initiation, transition and termination phases of bone remodeling. At the initiation phase, hemopoietic precursor cells are recruited to the basic multicellular unit and induced to differentiate into osteoclasts through cell-cell contact with osteoblasts. Bidirectional signaling occurs between ephrinB2 on osteoclasts and EphB4 on osteoblast precursor.

To test the effect of osteoclast precursors on mesenchymal cell differentiation, the osteoclast precursor cell line, RAW, was co-cultured with a mesenchymal cell line, C2C12. The cells were seeded in a 1:4 ratio using an osteogenic differentiating medium containing DMEM, L-glutamine, ascorbic acid, beta-glycerophosphate and dexamethasone. A culture of the C2C12 mesenchymal cell-line was used as a control.

Osteoblast differentiation was evaluated at day 10 using alkaline phosphatase staining as a marker (alkaline phosphatase staining kit from Sigma-Aldrich, St. Louis, Mo.). Cells were also stained with Alizarin red as a visual marker. Alkaline phosphatase and alzarin red was measured at 590 nm. FIG. 2 shows the results from these studies. Alkaline phosphatase (ALP) and Alizarin red (AR) were used to stain the cells. A: C2C12 control culture; AR. B: C2C12 control culture; ALP. C: C2C12 and RAW co culture (AR). D: C2C12 and RAW co culture; ALP. E: ALP absorbance at 590 nm. F: AR absorbance at 590. Unpaired Student T-Test was used to analyze the data.

Figure 2F:
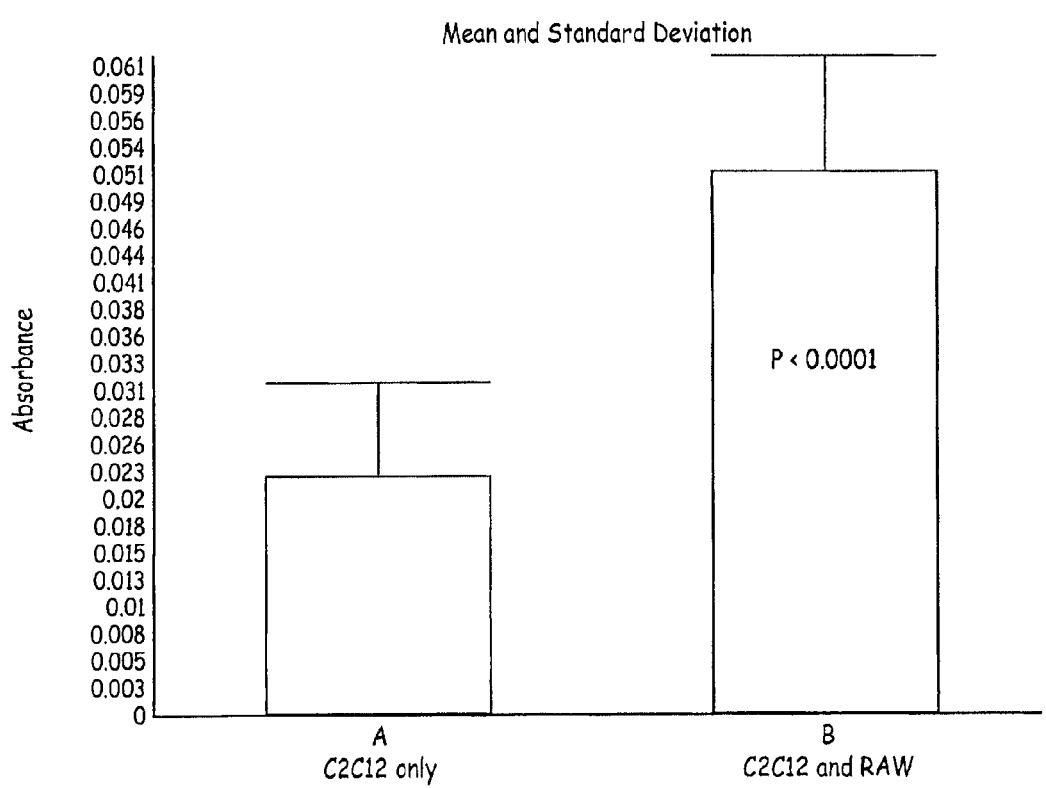
FIG. 2F depicts absorbance of RAW/C2C12 cultures as compared to the C2C12 only cultures after alkaline phosphatase staining.

Co-cultures of RAW and C2C12 cells (FIGS. 2C and D) showed significantly higher levels of alkaline phosphatase and Alizarin red staining as compared to the C2C12 control cultures (FIGS. 2A and B). Absorbance of the stained cultures was determined at 590 nm, and is depicted in FIGS. 2E and 2F. FIG. 2E is a graph of the alkaline phosphatase staining demonstrating a greater than 2-fold increase in absorbance measured in the RAW/C2C12 cultures as compared to the C2C12 only cultures.

These data suggest that the C2C12 mesenchymal cells, in the presence of the RAW osteoclast precursor cells, were induced to differentiate into osteoblast cells. Thus, seeding implant material with autologous osteoclast precursors will add osteoinductive features to the grafted material.

Example 2

Bone callus formation depends on osteoblastic new bone formation and osteoclastic resorption activity. During the remodeling phase, osteoclasts are very active. A major paradigm of osteoclast biology has emerged with the discovery of the receptor activator nuclear factor kB (RANK), its ligand (RANKL), and osteoprotegerin (OPG). These factors are heavily involved in bone resorption and in regulating osteoclast activity. RANK is a membrane receptor found on osteoclasts and some immune system cells. RANK binds to RANKL to promote differentiation, survival and activation of osteoclastic cells.

Recently, Marchelli et al demonstrated that in patients with atrophic nonunion shaft fractures, the mean serum OPG level was significantly increased with respect to healed and healing controls. The significantly higher serum OPG level in the patients may suggest an imbalance in the RANK/RANKL/OPG system, with concomitant osteoclast down-regulation. (Marchelli D, et al., J. Orthop. Traumatol. 2009 June; 10(2): 55).

Figure 3:
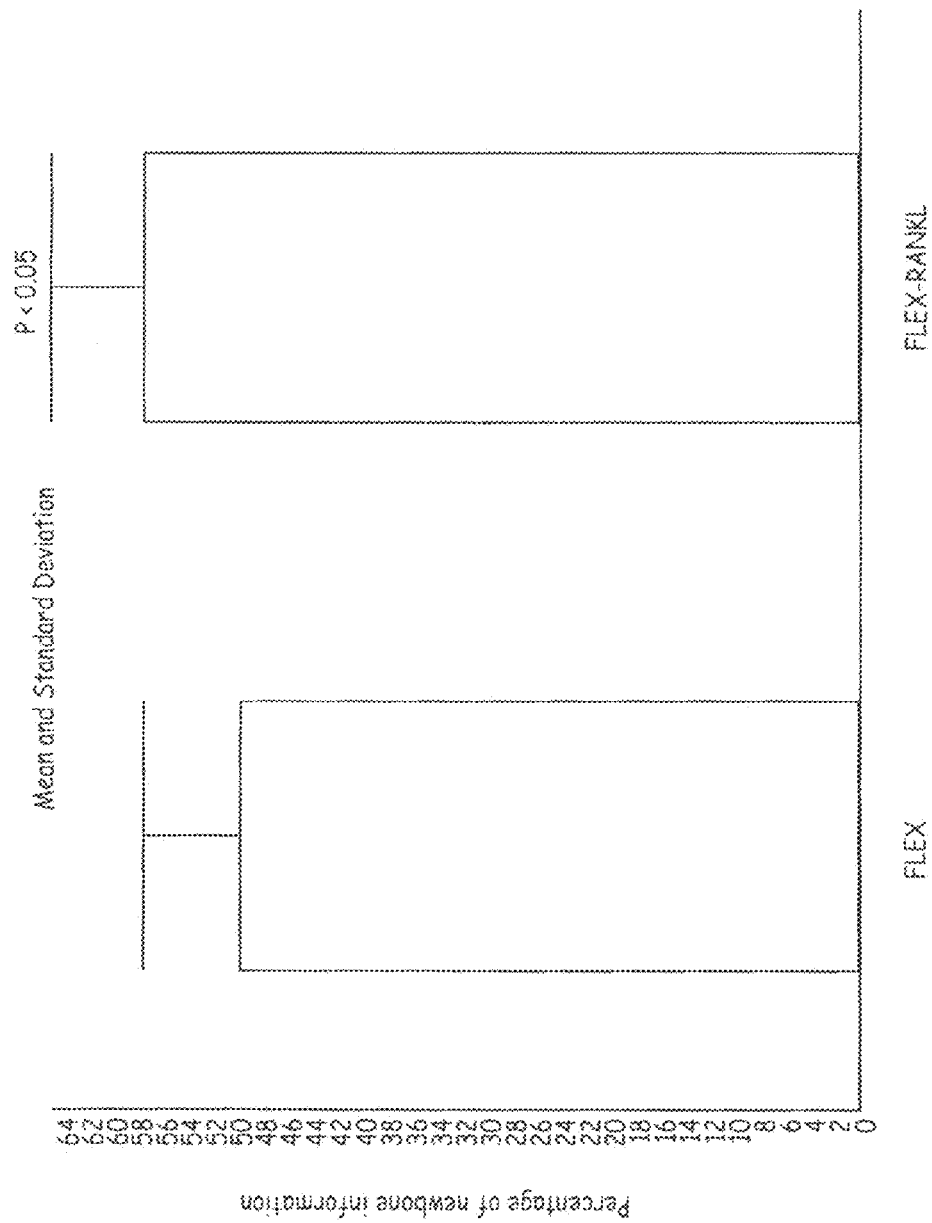
FIG. 3 Depicts the effect of RANKL on new bone formation in cortical defect in rat femur.

To test whether recombinant RANKL mixed with DBM may aid bone healing, a critical defect model was used in rat femurs. Three millimeter defects were created in femurs of athymic rats. The rats were divided into two groups, the bone defects from one group were implanted with 150 mg of Grafton® DBM FLEX (Osteotech, Eatontown, N.J.), the second group received Grafton® DBM FLEX mixed with two micrograms of recombinant RANKL. At three weeks, the rat femur defects were evaluated by MicroCT. As depicted in FIG. 2, the RANKL treated group demonstrated significantly ($p<0.05$) higher levels of new bone formation compared to control group (FIG. 3). Data was analyzed using paired student-t-test.

These results suggest that recombinant RANKL mixed with bone implant material can act as a stimulating substance for stimulating bone formation.

Example 3

Non-demineralized cortical bone is cut as a monolithic implant or pulverized to obtain particles. The material is soaked in MSCF solution to saturate adsorption and then lyophilized.

Example 4

Non-demineralized cortical bone is cut as a monolithic implant. IL-3 and hydrocortisone are combined with an alginate carrier to form a protein mixture. The non-demineralized cortical bone implant is coated with the protein mixture. The hydrogel coating is cross-linked with calcium ions.

Example 5

Calcium phosphate is combined with a polymer matrix. VEGF is encapsulated into polymer micro/nano particles. The VEGF-containing micro/nanoparticles are suspended in water or ethanol and then applied to the calcium phosphate.

Example 6

A monolithic implant is provided. It is formed by mixing partially demineralized particulated bone, a osteoclast stimulating factor, and a polymer matrix under critical or supercritical fluid such as carbon dioxide.

Example 7

Nondemineralized cancellous bone is particulated and mixed with glycerol. A mixture of MCSF and RANKL is added to the particulated cancellous bone glycerol combination. The resultant mix is loaded into a mold and compressed.

Example 8

Partially demineralized particulated cancellous bone is mixed with a glycerol carrier and applied to a calcium sulfate matrix. TNF-alpha is mixed with a collagen carrier to form a protein mixture. The protein mixture is applied to the partially demineralized particulate bone and calcium sulfate matrix.

Example 9

A hydroxyapatite implant is formed. MCSF and IL-1 are combined with a fucane carrier to form a protein mixture. The hydroxyapatite implant is coated with the protein mixture.

Example 10

A monolithic mineralized cortical bone implant is provided. PTH or PTHrP is added to a mixture of particulated demineralized bone matrix and a glycerol carrier. The monolithic cortical bone implant is coated with the mixture.

Example 11

Surface demineralized particulated cortical bone is combined with plasmid DNA. PTH PTHrP plasmid is either directly loaded onto particulated bone by coating or first encapsulated into polymer micro/nano spheres and then mixed with surface demineralized cortical bone.

Although the invention has been described with reference to various embodiments, persons skilled in the art will recognize that changes may be made in form and detail without departing from the spirit and scope of the invention.

What is claimed is:

1. An implant for promoting bone formation comprising: an implantable material; and a stimulating substance, wherein the stimulating substance stimulates osteoclast formation and comprises osteoclast precursor cells and the implant comprises mesenchymal stem cells, the mesenchymal stem cells and the osteoclast precursor cells in a ratio of 1:4.

2. The implant of claim 1, wherein the material is mineralized bone.

3. The implant of claim 1, wherein the material is hydroxyapatite.

4. The implant of claim 1, wherein the material is a calcium phosphate material.

5. The implant of claim 1, further comprising a second stimulating substance, wherein the second stimulating substance stimulates osteoblast formation or recruitment in vivo.

6. The implant of claim 1, further comprising a second stimulating substance, wherein the second stimulating substance enhances resorbing activity of osteoclasts in vivo.

7. The implant of claim 1, wherein the stimulating substance further comprises one of RANKL, MCSF, ADAM-12, PTH, PTHrP, VEGF, hydrocortisone, 1,25 dihydroxyvitamin D3, PGE2, TNFalpha, IL-1beta, IL-3, IL-6, IL-11, and bFGF.

8. The implant of claim 1, wherein the stimulating substance is a DNA that encodes one or more of RANKL, MCSF, ADAM-12, PTH, PTHrP, VEGF, PGE2, TNFalpha, IL-1beta, IL-3, IL-6, IL-11, and bFGF.

9. The implant of claim 1, wherein the implant is load-bearing.

10. The implant of claim 1, wherein the implantable material comprises large segmental allograft pieces.

* * * * *